United States Patent [19]

Ligler et al.

[11] Patent Number: 5,183,740
[45] Date of Patent: Feb. 2, 1993

[54] FLOW IMMUNOSENSOR METHOD AND APPARATUS

[75] Inventors: Frances S. Ligler, Potomac; Gaber Bruce P., Bethesda, both of Md.; Anne W. Kusterbeck, Falls Church; Gregory A. Wemhoff, Manassas, both of Va.

[73] Assignee: The United States of America as represented by the Secretary of the Navy, Washington, D.C.

[21] Appl. No.: 486,024

[22] Filed: Feb. 23, 1990

[51] Int. Cl.$^5$ .................... G01N 33/53; G01N 33/569
[52] U.S. Cl. .................... 435/7.32; 435/7.33; 435/7.34; 435/7.36; 435/7.92; 435/7.93; 435/961; 435/968; 436/518; 436/529; 436/538; 436/541; 422/70; 422/82; 422/82.05
[58] Field of Search .................... 435/7.36, 7.1, 7.92, 435/7.93, 805, 968, 961, 967, 7.32, 7.33, 7.34; 436/518, 529, 538, 541, 800, 801, 804; 422/70, 82, 82.01-82.09

[56] References Cited

U.S. PATENT DOCUMENTS

| 4,264,327 | 4/1981 | Blum | 422/82 X |
| 4,277,560 | 7/1981 | Gray et al. | 435/7.93 X |
| 4,582,809 | 4/1986 | Block et al. | 422/82.08 X |
| 4,803,170 | 2/1989 | Stanton et al. | 436/518 |
| 4,895,809 | 1/1990 | Schlabach et al. | 436/518 |

FOREIGN PATENT DOCUMENTS

| 0210107 | 1/1987 | European Pat. Off. | 435/7.93 |
| 0296036 | 12/1988 | European Pat. Off. | 435/7.93 |

OTHER PUBLICATIONS

E. Maggio (ed), Enzyme-Immunoassay, (CRC Press, Inc. Boca Ratio, Fla.) pp. 224-233, 243, 289 (1980).
Kelly, "Separation-Free Enzyme Fluorescence Immunoassay by Continuous Flow Injection Analysis" in Enzyme-Mediated Immunoassay, (Plenum Press 1985) 191-201.

Primary Examiner—Esther L. Kepplinger
Assistant Examiner—Carol A. Spiegel
Attorney, Agent, or Firm—Thomas E. McDonnell; Barry A. Edelberg

[57] ABSTRACT

A method of detecting a target moiety comprising the steps of (a) providing an antibody specific to the target, (b) saturating the binding sites of the antibody with a labelled form of the target, (c) flowing a liquid containing the target past the saturated antibody, thereby (d) allowing the target to displace the labelled antigen, and (e) detecting the displaced labelled antigen with a detector for the label.

Also, the invention is accomplished by a flow immunosensor comprising: a liquid flowing through the immunosensor for moving a sample through the immunosensor; a receiving means for introducing the sample to the liquid stream; a flow control means for moving the liquid stream through the immunosensor; an exchanger connected to the sample receiving means in which the sample is brought in contact with labelled antigens of the target and whereby any target present is allowed to displace the labelled antigen; a detection apparatus connected to the exchanger for detecting any labelled antigen which is released; and a disposal means connected to the detection apparatus for disposing of or collecting of waste coming from the detection apparatus.

12 Claims, 3 Drawing Sheets

A = 8.0 ug/ml Lysine (44 μM or 1.6 μg loaded)

B = 25 ng/ml DNP-lys (72 nM or 5 ng loaded)

C = 50 ng/ml DNP-lys (140 nM or 10 ng loaded)

D = 100 ng/ml DNP-lys (290 nM or 20 ng loaded)

E = 200 ng/ml DNP-lys (580 nM or 40 ng loaded)

FLOW IMMUNOSENSOR METHOD AND APPARATUS

BACKGROUND OF THE INVENTION

1. Field of the Invention

This invention relates to a continuous and relatively instantaneous antibody-based method for detecting a target moiety and a flow immunosensor apparatus capable of conducting the method.

2. Description of the Prior Art

Today, for reasons of health and safety, it is necessary to be able to rapidly detect the presence of moieties in an environment or samples which are themselves dangerous or are associated with materials which can be dangerous. These moieties may be in a medicine, a food or a sample of body fluid. In addition, these moieties can be in the air or water. The moieties are referred to herein as a target or target moiety.

The target may be something dangerous to health such as a toxic material present in a food, or a toxic agent present in the air or in the water supply. In addition, the target can be a chemical indicating the presence of something dangerous to human welfare such as vapors exuded by explosives and illicut drugs. Further, the target can be a specific component or metabolite found in animal body fluids. These later targets can indicate presence of disease or simply a physical condition.

Many tests are available or proposed for detecting target moieties under laboratory conditions. Toxins in food or water are detected by chemical tests conducted on a batch basis. In addition, toxins in air or water can be detected by continuous processes but, to date, these processes need a relatively large target sample to accomplish the purpose. In addition, the tests do not distinguish between or are blind to many targets. Many batch tests exist for the detection and identification of metabolites or components of body fluids. Most of these tests do not provide substantially instantaneous answers or rapid while-you-wait answers.

Real-time tests are defined here as tests which will provide an answer within two or three minutes of a sample being taken and introduced to the test. Tests which require removing a sample from an environment and subjecting it to multiple handling and transfer operations with developing or incubation time for a reading are not considered real-time tests. As an illustrative example only, removal of a sample from a flowing air or water stream and providing an answer in less than a minute so that the conditions indicated by the test are indicative of the conditions in the environment is considered a real-time test.

Two areas of high interest today are the detection of drugs and the detection of explosive materials. Although the chemical problems for detecting these two types of materials are markedly different, the physical problems are often the same. Both require real-time tests. Similarly, there is also a need for a real-time method of detecting the presence of a moiety in a sample-by-sample situation so a sample can be quickly characterized and appropriate action taken. This might be a simple qualitative test at a crime scene to identify a sample as a drug, a sample as blood, or a sample as semen.

As acts of terrorism, bombs have been placed aboard aircraft or in buildings. Explosive devices are usually hidden in samll, enclosed and restricted spaces. Defense against such acts requires detection of the explosive materials in the hiding place. Similarly, illegal drugs are smuggled into a country, building or other secured area by being hidden in small, enclosed and restricted spaces. The vapor pressure of most drugs and explosives is such that very small amounts are available for detection by sampling air. Detection of such small amounts of target vapors of specific targets requires discriminating and sensitive equipment, test methods and materials.

U.S. Pat. No. 4,818,870 to Griffith et al. describes an air sampling probe used with "sniffer" devices. These devices attempt to detect vapors from drugs and explosives. The detector in Griffith's invention is a mass analyzer. U.S. Pat. No. 4,866,439 discloses a means for detecting explosives using an electron capture detector. U.S. Pat. Nos. 4,849,628; 4,776,409 and 4,884,839 describe atmospheric samplers which are ionization sources or photoionization detectors. In U.S. Pat. No. 4,360,776, Bauman describes the use of antibodies in an electron spin resonance technique to detect target agents.

Monoclonal antibody technology has markedly changed modern chemical and medical analytical techniques. Since monoclonal antibody technology has made highly specific antibodies available in large quantities, columns containing supports coated with antibodies have come into general use for the purification of antigens.

Antibody-based detection systems such as ELISAs (Enzyme Linked ImmunoSorbent Assays) and radioimmunoassays have been developed to take advantage of antibody specificity and sensitivity. However, while sensitive, these techniques are time-consuming and usually require multiple manipulations and/or reagent additions. Antibodies, due to their inherent sensitivity and selectivity, are natural candidates for use as the detection element in biosensors.

Biosensors incorporating antibodies have been classified as immunosensors. Most of the immunosensors reported to date (Ives et al, *Applied Biotechnology Laboratory*, Mar. 10, 1989; Andrade et al., U.S. Pat. No. 4,368,047 (1983); Place et al., *Biosensors*, 1, 321 (1985); Tromberg et al., *Anal. Chem.*, 59, 1226 (1987); Thompson, R. B. and F. S. Ligler. NRL Memorandum Report 6182, 1988) rely on the association of antibody with antigen and are configured as direct binding or sandwich assays for detection of large molecules or as competition assays for the detection of small molecules.

The widespread use of ELISAs and affinity chromatography have stimulated theoretical consideration of the kinetics of antigen-antibody binding at the solid-liquid interface (Lew, J. *Immunol. Methods*, 72, 171 (1984); Lundstrom et al., *J. Theor. Biol.*, 110, 195 (1984); Nygren et al., *J. Immunol. Methods*, 101, 63 (1987); Stenberg et al., *J. Immunol Methods*, 113, 3 (1988)). The rate of association for antigen and antibody is determined to be a function of the density of the immobilized component, antibody affinity, geometry of the substrate, and concentration of the free component. In the studies cited above, the antigen is bound to the surface and the antibody is free in solution.

For multivalent systems, Stenberg et al. (1988), cited above, have shown that the association rate of antibodies and antigens at the surface of macroscopic particles is limited by the diffusional mass transfer as long as the surface reaction is fast compared to the diffusion rate. In the diffusion limited region, the rate is inversely proportional to the sphere radius.

Ives et al. (1989), cited above, briefly discuss the displacement of a labelled antigen by an excess of unlabelled antigen under the assumption that it is an equilibrium exchange reaction. As long as the antigen is monovalent and of low molecular weight, Ives et al. concludes that the exchange will require 15-20 minutes.

For an antigen-antibody interaction, the dissociation rate is normally considered to determine the strength of binding. For dissociation of IgG and Fab' antibodies from immobilized antigens, rate constants in the range of $10^{-4}$–$10^{-5}$ sec$^{-1}$ have been obtained (Liu et al., *IEEE Trans. of Biomedical Eng.*, Vol. BME-33, No. 2, February 1986; Nygren, 1987, cited above; Mason et al., *Biochem. J.*, 187, 1 (1980); Werthen et al., *J. Immunol. Methods*, 115, 71 (1988)). For the time intervals typical of immunoassay, the binding can thus be considered as irreversible.

In the studies of Nygren (1987), cited above, over a course of several hours, the only dissociation seen of antibody bound to immobilized antigen was in the presence of excess antigen. The displacement of bound antigen from antibody affinity columns upon the addition of excess free antigen is also well known.

Aizawa et al., *Transducers '87*, 783 (1988), report "remarkable" displacement of peroxidase-labelled IgG antibody from immobilized antigen using micromolar quantities of free antigen. Aizawa et al.'s report was incomplete because neither the time nor the ratio of antibody to free antigen was reported.

The hit-and-run immunoassay (Warden et al., *Anal. Biochem.*, 162, 363 (1987) is an immunoassay also conducted on a column support. A problem with this hit-and-run assay is that it is not a continuous flow system. When antigen is introduced to the column, it is allowed to remain there for 5 minutes. Thus in a 5-minute period, only one column volume of sample can be tested. Also, during this time, diffusion rather than flow rate determines the number of antigen-antibody encounters. In addition, antigen is immobilized on the column and a fluorescent marked Fab' fragment of IgG is bound to it. This Fab' fragment is claimed to be in an equilibrium-binding condition so that it is continually bound to individual immobilized antigens, released, and rebound. When sample containing antigen is introduced, the released Fab' fragment binds to it over the 5-minute period and the soluble fluorescent complex flows downstream to the fluorescence detector.

Antibodies have been applied to the detection of illicit drugs and explosives. In U.S. Pat. No. 4,353,886, Lukens et al. describe a field test for narcotic vapors. The test uses antibodies mounted on a test plate to detect the vapor. The test is a batch type system requiring the exposure and development of different plates. The system can not continually monitor an environment.

Many techniques have been developed for detecting drugs either singularly or in groups. In U.S. Pat. No. 4,235,864, Kanul et al. describe a method of detecting and identifying multiple drugs found together. A raiolabelled conjugate of ecgonine is used to detect cocaine in a traditional radioimmunoassay. Methods for the preparation of the antibodies for many of the illicit drugs are well known and some are available from commercial sources.

The existing techniques using antibodies do not have the capability to continually monitor an environment or provide a response in real time. Existing systems are semi-batch processes depending on direct binding, competitive binding, or equilibrium exchange reactions.

SUMMARY OF THE INVENTION

Accordingly, an object of this invention is a method of detecting a target in real time.

Additionally, an object of this invention is a method for monitoring an environment in real time to detect a target.

Another object of the invention is a method sensitive to the detection of small quantities of target agent.

Yet another object of the invention is a portable immunosensor capable of detecting a target in real time.

A further object of the invention is an immunosensor which operates in real time in a continuous flow mode.

Another object of the invention is an immunosensor capable of detecting both high and low (hapten) molecular weight targets in real time.

These and additional objects of the invention are accomplished by a method of detecting a target moiety comprising the steps of (a) providing an antibody specific to the target, (b) saturating the binding sites of the antibody with a labelled form of the target, (c) flowing a medium containing the target past the saturated antibody, thereby (d) allowing the target to displace the labelled antigen, and (e) detecting the displaced labelled antigen with a detector for the label.

Also, the invention is accomplished by a flow immunosensor comprising: a liquid stream flowing through the immunosensor for moving a sample through the immunosensor; a receiving means for introducing the sample to the liquid stream; a flow control means for moving the liquid stream through the immunosensor; an exchanger connected to the sample receiving means in which the sample is brought in contact with labelled antigens of the target and where any target present is allowed to displace the labelled antigen; a detection apparatus connected to the exchanger for detecting any labelled antigen which is released; and a disposal means connected to the detection apparatus for disposing of or collecting of waste coming from the detection apparatus.

The exchanger comprises a chamber containing a support medium. An antibody is immobilized on the support medium. The antibody recognizes with specificity and sensitivity the target. A labelled antigen is bound by the immobilized antibody. Any label used in the art is applicable here, but radiological or fluorescent labels are preferred. The labelled antigen is capable of being displaced in the presence of the target.

The detection apparatus will be different for each type of label. When the label is a radiolabel, the detector contains, at least, a radiation sensor to detect and display the quantity of radiation detected. If a fluorescent label is used, the detection apparatus contains at least a light source for exciting the fluorophore-labelled antigens to fluoresce and a reading means for detecting and displaying the quantity of fluorescent light generated.

The apparatus also includes a reservoir to hold the liquid which forms the liquid stream and transports samples through the method and apparatus. Lastly, the immunosensor contains a means of disposing of or recycling the fluid flowing through the system.

BRIEF DESCRIPTION OF THE DRAWINGS

A more complete appreciation of the invention will be obtained by reference to the following Description of the Preferred Embodiments and the accompanying

DESCRIPTION OF THE PREFERRED EMBODIMENTS

Figure 1:
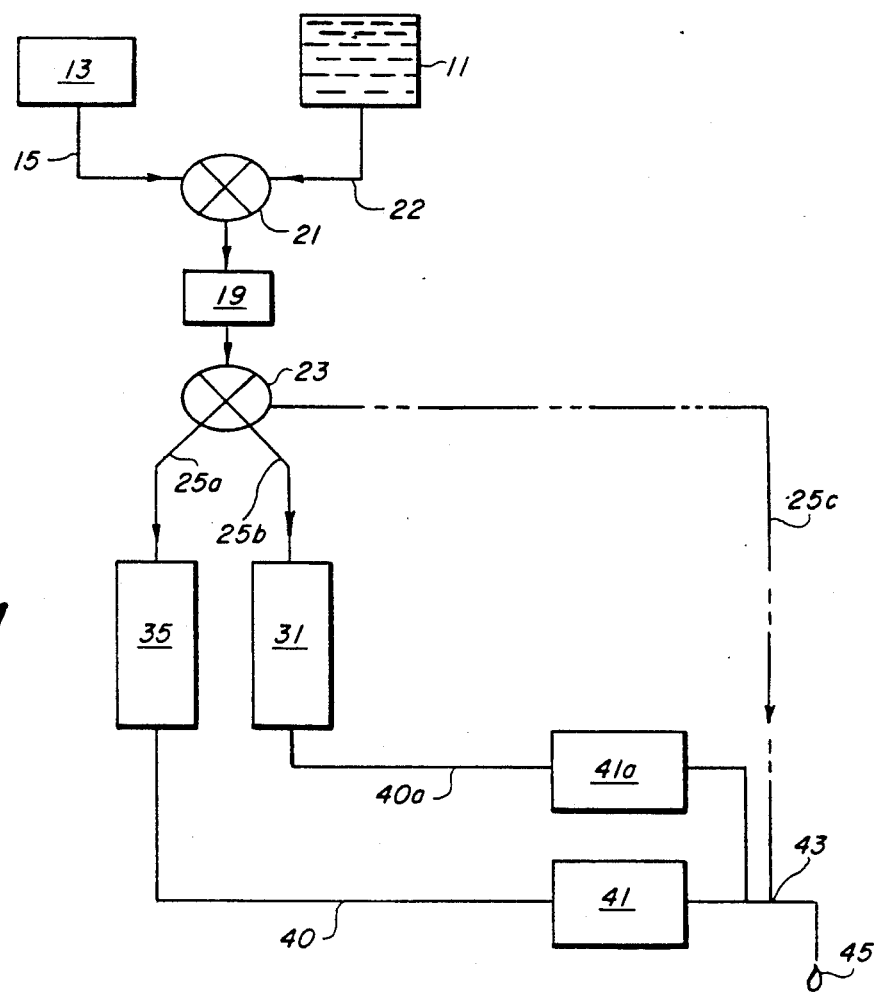
FIG. 1 is a schematic plan of an apparatus forming embodiments of the invention.

Antibodies, because of their inherent specificity, are natural candidates for use as the detection element in biosensors. Biosensors utilizing antibodies are classified as immunosensors.

The method and immunosensor of this invention are believed to operate through a different mechanism than is associated with existing methods and immunosensors. The term "immunosensor" is used here to refer to the part of the invention as it is embodied in an apparatus or device.

The binding of antigen to immobilized antibody is considered to be essentially irreversible within the first few hours (Stenberg et al., *J. Immunol. Methods,* 113, p.3 (1988)). It was therefore surprising to find that low levels of antigen (relative to moles of antibody) could be detected in a continuous flowing stream of liquid.

In the method of the invention, the displacement of the labelled antigen occurs under non-equilibrium conditions in seconds. It is hypothesized that the mechanics of the reaction do not follow those described for immobilized antigen/antibody complexes in static systems. The detection method is based on the displacement of a pre-bound labelled complex with a similar or equivalent antigenic site and not solely on the binding of antigen to the column. The displacement reaction may not reflect simple equilibrium binding of the prior art as the target molecule is not allowed sufficient time in the vicinity of the antibody/labelled-antigen complex to allow equilibration to occur. The method and immunosensor of this invention rely on the dissociation of antigen from the antibody binding site instead of the association of antibody and antigen.

Ives et al. (1989), cited above, briefly discuss the displacement of a labelled antigen by an unlabelled antigen under the assumption that it is an equilibrium exchange reaction. As long as the antigen is monovalent and low molecular weight, Ives et al. conclude that the exchange will reach completion in 15-20 minutes. In the system described here, the displacement occurs in seconds.

The goal of the method and immunosensor, also referred to as a flow immunosensor, of this invention is to provide an almost instantaneous indication of the presence of a target by continuously monitoring an environment for the presence of a specific chemical or biological species (antigen). The method and immunosensor can be used to monitor for more than one chemical or species at a time.

The invention is not limited to situations where the flow of suspect material is expected on a continuous basis. The concept of the invention lies in being able to monitor an activity in real time instead of removing a sample from the on going "stream" and analyzing it separately. Of course, the method and device of this invention can be used to analyze or check a specific sample or multiple discrete samples on a sample-by-sample basis by injecting the samples into the liquid flow stream. In other words, single or multiple samples can be processed by the method of this invention in the immunosensor of this invention to obtain rapid analyses of the samples.

Generally, the method of this invention involves flowing a stream of liquid from a sample receiving means through an exchange area which contains a labelled antigen bound to an immobilized antibody specific for the target. The antigen and antibody are such that they do not react with the flowing liquid. Following the pass through the exchange area, the liquid passes through a detection apparatus capable of detecting the label on the labelled antigen if any.

To operate the method, a sample is injected into the liquid flow stream and passes through the exchange area. Alternatively, the sample can be dispersed in a volume of liquid and this volume of liquid introduced into the flowing stream as the sample. In yet another alternative embodiment, the sample is dispersed in a volume of liquid and the volume of liquid is used as the liquid flow stream. If the sample contains a target, the target will displace the labelled antigen which will flow in the liquid stream through the detection apparatus where it will be detected. The liquid, with or without a sample, flows from the detection apparatus to a disposal or recovery area where it is appropriately dealt with.

The liquids used in this invention are water, buffers, and aqueous sample diluents. Preferred liquids are buffers such as phosphate-buffered saline, borate-buffered saline, TRIS-saline, Alseiver's and Ringer's. The buffers for biological uses are described generally in this booklet "Buffers", edited by Donald Guoffrey, published by American Hoechst Corporation La Jolla, CA (1983). The exact liquid is not critical to the invention as long as the liquid is a solvent for the target and reagents used in the process and as long as the liquid does not chemically react with the target or reagents of the method or the components of the immunosensor apparatus.

The flow rate of the liquid stream in the method of this invention should be between 0.1 and 2.0 milliliters per minute, preferably between 0.3 and 0.8 milliliters per minute. The optimum flow rate is such that the residence time of the target on the exchanger is sufficient to generate displacement of measurable quantities of labelled antigen in the shortest possible time.

An extensive range of antibodies applicable for use in this invention are commercially available or can be made from descriptions of methods of preparation available in the literature. Linscott's Directory provides the most complete single listing of commercially available antibodies ("Linscott's Directory", 40 Glen drive, Mill Valley, CA 94941). Any antibodies described in the literature can be employed or adapted to the method and immunosensor of this invention for identification of a wide range of targets.

The method can be used to detect specific components of body fluids such as thyroxine, high density lipoprotein, low density lipoprotein, cholesterol, albumin, alpha-1 antitrypsin, beta-2 microglobulin, ceruloplasmin, C1 inhibitor, C1q and other complement components, C-reactive protein, cryofibrinogen, ferritin, meylin basic protein, transferrin, insulin, human chorionic gonadotropin, estrogen, progesterone or antigens shed from pathogens such as, *H. influenza, N. meningitides, S. pneumonia, Bordefella pertussis, Borrelia burgdorferi* (Lyme's disease), staphlococcus, and streptococcus.

An important function of the method and immunosensor of this invention is that determinations can be made in real time. This permits the instant evaluation of a sample for body fluids and therapeutic drugs and drugs of abuse such as theophylline, digoxin, L-dopa, insulin, cocaine and its metabolites, cannibis metabolites, heroin or morphine metabolites. These therapeutic drugs and drugs of abuse can be monitored on a sample-by-sample basis by injecting or dissolving a sample into a stream flowing through an exchanger containing the appropriate antibody and labelled antigen.

Most importantly, the environment, such as the surrounding air or water, can be monitored continually for traces or vapors of dangerous materials and other substances sch as illicit drugs, various explosives such as trinitrotoluene (TNT), cyclonite (RDX), pentaerythritol tetranitrate (PETN) or other explosives, biological or chemical warfare agents, toxins, nitrobenzenes, isothiocyanates, and other water and air pollutants.

The method and immunosensor of this invention may also be used to monitor fermentation processes or enzymatic conversion of substrates.

A major advantage of this method is that reagents, other than the flowing fluid, are not exhausted unless a positive result, which can be referred to as a "hit", is detected. With the proper design of the apparatus to automate this method, the buffer can be recycled until there is a "hit". Following a "hit" the exchange area can be replaced or regenerated.

To regenerate the exchange area, fluid containing and excess of the labelled antigen is introduced into the exchange area. The labelled antigen will exchange with the unlabelled target and saturate the antibody binding sites. Because the regeneration is an equilibrium exchange reaction, the concentration of the labelled antigen in the buffer should be as high as possible and the dwell time of the labelled antigen in the exchange area should be as long as possible to favor a complete exchange.

The flow immunosensor and method rely on the reversibility of the antigen-antibody binding. The labelled antigen complexes can have a variety of chemical compositions as long as water-solubility is maintained. The antigenic site on the labelled molecule does not have to be identical to the antigen to be detected. A modification to the labelled antigen which does not inhibit antibody binding but decreases binding affinity may actually enhance the displacement reaction, and consequently the sensitivity of the system.

Any label which can be rapidly detected without a "development" time can be used. Labels include but are not limited to radiolabels, fluorophores, chromophores, electroactive groups, and electron spin labels. Preferred are radioactive labels and fluorescent labels. Because of the difficulties in disposing of radioactive waste materials, fluorescent labels are most preferred.

Two features of the fluorescent-labelled antigen complex are critical to maximizing the sensitivity. First, the fluorescent antigen complex must not stick directly to the column matrix or any of the components in the flow path. Second, for highest sensitivity only one antigenic site per fluorophore-labelled molecule is preferred. Complexes containing multiple antigenic sites may be used, but sensitivity may not be as great.

The principal parts of the flow immunosensor are (1) the column and support medium containing immobilized antibodies for specific biochemical recognition of the antigen of interest, (2) the labelled antigen complexes, and (3) the flow system monitor or detector. Of course, ancillary equipment such as connecting tubing, a pump, and valves, is needed to make a fully operable immunosensor apparatus, but the means of connecting such ancillary equipment is done in the usual manner once the principles of this invention are seen. The specific components must be made of materials which will not interact or contaminate the reagents of the method of this invention. As needed and in the manner known in the art for such devices, computer hardware and software can be added to automate the system.

FIG. 1 is a schematic drawing which can be used to represent different configurations of the system. Fluid is contained in reservoir 11. The fluid flows from reservoir 11 through tubing 22 and through suitable control valve 21 to a suitable pump 19. The pump 19 is of the type which can move relatively small volumes of liquid at a steady flow rate through the system without contaminating the system.

A sample receiving means 13 is also connected through tubing 15 to the valve 21. The receiving means can take multiple forms depending on the specific application of the immunosensor. In one embodiment, 13 can be a fluid container in which samples are dissolved and fed into the apparatus as the liquid of the system or, in smaller volumes of liquid, as a sample which is added to the liquid stream coming from the reservoir 11 as by a syringe or injector loop. In an alternate embodiment, the sample receiving means can be in the form of a liquid "sipper" or an air sample (such as the Spincon ® made by the Midwest Research Institute) which continually monitors the environment and brings samples of the environment into the liquid stream flowing through tubing 22.

From the pump 19, the fluid flows through valve 23 into tubing 25a, b, and/or c. The valve 23 can be a diverter valve to switch flow between column 35 and column 31 or the dump 45 or, in an alternative embodiment, 23 can be a splitter valve which divides the liquid flow between 35 and 31. The column 31 is not an absolute necessity but is a preferred embodiment in the interest of control against false positive signals. A drain 45 can connected to the valve 23 through tubes 25c and 43 to divert flow from the columns 35 and 31 or as a means of draining the system. In the preferred form of the immunosensor, the valve 23 splits the sample between the exchange column 35 and the control column 31. The exchange column 35 and the control column 31 are not necessarily of one specific shape but can be a tube, column or vessel of any shape which contains a support medium 33 and provides a flow path for the liquid stream to contact the support and the antibodies immobilized on the support.

The volume or form of these columns 35 and 31 is not critical as long as it allows good contact time between the sample and the labelled antigens and does not interact with the label, targets or other materials in the immunosensor or method. It is preferred to use a column, preferably made of chemically inert, rigid material such as glass, teflon, or stainless steel. The volume of liquid held in the column is not critical but, to make the use of replaceable micro-columns the preferred structure, volumes of 0.1 to 0.5 ml are preferred. The flow immunosensor can be made small and portable. Columns of approximately 200 μl bed volume are sufficient for most applications.

The support medium 33 must be a material which is neutral to the materials being analyzed so the support medium does not create false positive or false negative signals. A preferred material is activated polysaccharide beads such as SEPHAROSE® beads obtained from Sigma. Among other suitable materials are silica or glass beads, hollow fibers or activated polymers. The support medium is present in both the exchange column 35 and the control column 31. In a further alternative embodiment, hollow fibers or bundles of capillary tubes may serve simultaneously as tubes and support medium. The surface area of the tube acting as support and the passages in or around the bundles acting as the pass through for the fluid.

An antibody 37 is bound to support medium 33 and is saturated with a labelled antigen 39. The exchange column 35 will contain an antibody and antigen for the target. The control column 31 will contain an antibody and antigen for a target which is not likely to be in the sample. The label, support, and column materials are otherwise the same in both exchange column 35 and control column 31.

Figure 2:
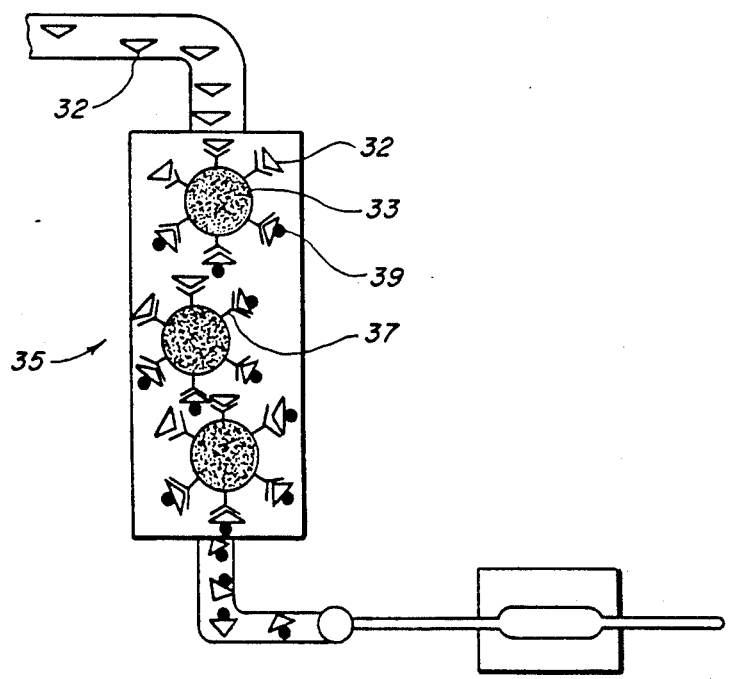
FIG. 2 is a schematic detail of an exchanger of an embodiment of the invention.

As illustrated in FIG. 1 and 2, in operation, target antigen enters the exchange column 35 and displaces the labelled antigen 39 from the antibody 37. The displaced labelled antigen 39 flows out of the column 35, through tubing 40 to the detector 41 where its presence is detected. The waste 45 is conducted away by tubing 43 and disposed of or recycled, as appropriate. At the same time the control sample flows through the control column 31, contacts the non-responsive antibodies and then flows through tubing 40a to a second detector 41a where no signal is expected. The flowing control liquid can be disposed of or recycled through 43 and 45 in like manner to the liquid flowing through column 35.

The detector 41 and its sister 41a can be a fluorimeter, spectrophotometer, radiation detector, or electrode, but is preferably a fluorimeter equipped with a flow cell and microprocessor for flow control, data processing, and signal generation.

Execution of the displacement reaction within the column involves the following steps: Antibodies immobilized on the solid support, 33, are first exposed to an excess of antigen which has been labelled so that labelled molecules occupy the available binding sites of the antibodies. The antibody-coated support and labelled antibody are loaded into 200 μl columns and washed with buffer until the baseline is stable. Typical flow rates used with the system are 0.3-0.8 ml/min. When the test sample containing the (unlabelled) antigen is passed over the column, labelled antigens are released from the binding sites on the immobilized antibodies, generating a signal that is proportional to the concentration of the antigen in the sample. The signal is detected as the labelled complexes flow downstream through a detector equipped with a flow cell.

The columns are designed to be small, inexpensive and interchangeable, allowing the column to be discarded or regenerated by flushing with excess labelled antigens. This renewal capacity allows periodic testing of the system by introducing "standards" of dissolved antigen to make certain that positive signals are being generated. Columns including irrelevant antibodies and the corresponding labelled molecules can be used to control for false positive signals (column 31, FIG. 1). The sample stream can be split (valve 23, FIG. 1) to pass through this control column as it passes through the exchanger column. Any factor (i.e. heat, organic solvent) which might cause nonspecific release of antigen from antibody would trigger a signal from the control column as well as from the exchanger column.

The current version of the device incorporates a briefcase-sized fluorimeter obtained from Spectrovision, but that portion of the device can be made even smaller. Small lasers can also be incorporated into the fluorimeter to increase sensitivity. As an option, a microprocessor has been added to control the valves and pump, process the data, and generate a data output.

In addition to monitoring a continuous stream for the presence of antigen, the exchanger column can be used in conjunction with the automated assay of large numbers of discrete samples. For example, automated samples ("sipper") exist which can extract fluids from 96-well microtiter plates or arrays of tubes and introduce them into a fluid stream. When used in conjunction with the immunosensor described above, large numbers of discrete samples could be screened very quickly.

The immunosensor of this invention has several characteristics which make it an attractive alternative to competitive immunoassay for the detection of small molecules. First, picomoles of antigen can be detected under continuous flow rates as fast as 0.8 ml/min. There is no absolute requirement for the flow to be stopped so that the antigen displacement reaction can occur. Second, the displacement reaction produces a signal in contrast to many competitive immunoassays where the disappearance of signal is measured. It is easier to detect the appearance of signal than to detect a small decrease in signal. Third, the sensor itself can be made relatively small and convenient for continuous monitoring or screening of large numbers of samples. There are no reagents to add, mixing steps to execute, or manipulations to be done during the assay. Finally, the method and immunosensor are adaptable for detection of a wide range of targets, including small as well as large molecules.

Having described the invention, the following examples are given to illustrate specific applications of the invention including specific techniques which can be used to perform the invention. These specific examples are not intended to limit the scope of the invention described in this application.

EXAMPLE 1

Detection of Dinitrophenol (DNP)

Antibody was coupled to tresyl chloride-activated SEPHAROS® 4B (Sigma Chemical Co., St. Louis, Mo.) using standard procedures. The amount of protein bound to the support was determined using a Coomassie blue assay following the modifications outlined by Ahmad and Saleemuddin (*Anal. Biochem*, 148, pp. 553-541 (1985)) for the determination of protein concentrations on solid supports. The available antigen-binding sites of the immobilized antibody were reacted with the radiolabelled or fluoresceinated DNP conjugates by incubation with the SEPHAROSE® at least overnight at 4° C. on a rocking platform. In these examples, the conjugate consisted of DNP coupled to tetrasulfonated Insulin A-chain (described in a related patent application by Bredehorst, Ligler, Kusterbeck Wemhoff and Vogel, titled Ligand-Label Conjugates Which Contain Polyoxoanions of Sulfer or Phosphorus, now U.S. Ser. No. 07/512,272, filed Apr. 20, 1990). The DNP conjugates were added at a molar ratio of DNP to antibody of 3-to1. Immediately prior to use an aliquot of the slurry was removed, spun in microcentrifuge for 30 sec., the supernatant removed, and the SEPHAROSE ® resuspended in phosphate buffered saline with 0.1% v/v TRITON ® X-100, a non-ionic, polyoxyethylene surfactant, (10 mM phosphate, 0.15M saline, this is the system buffer used throughout the assay). For storage, sodium azide, 0.1% v/v, was added to the medium to inhibit bacterial growth.

The radioimmunoassays were performed using columns with a bed volume of 500 μl. The fluoroimmunoassays were performed using columns with a bed volume of 200 μl of the prepared SEPHAROSE ®. The columns had a 7 mm inside diameter and a glass frit at the column exit. The buffer flow was established using a peristaltic pump connected downstream from the column and, where applicable, downstream from the fluorimeter. When discrete aliquots of the column effluent were collected, they were assayed on a scintillation counter or an SLM 8000 fluorimeter equipped with a 200 μl cuvette. For continuous monitoring the effluent was directed to a Spectrovision fluorimeter equipped with an 8 μl flow cell and the PMT (photomultiplier tube) high voltage set at 900 volts. Both the SLM 8000 and the Spectrovision fluorimeters were equipped with a 515 nm bandpass filter for the emission light.

Figure 3:
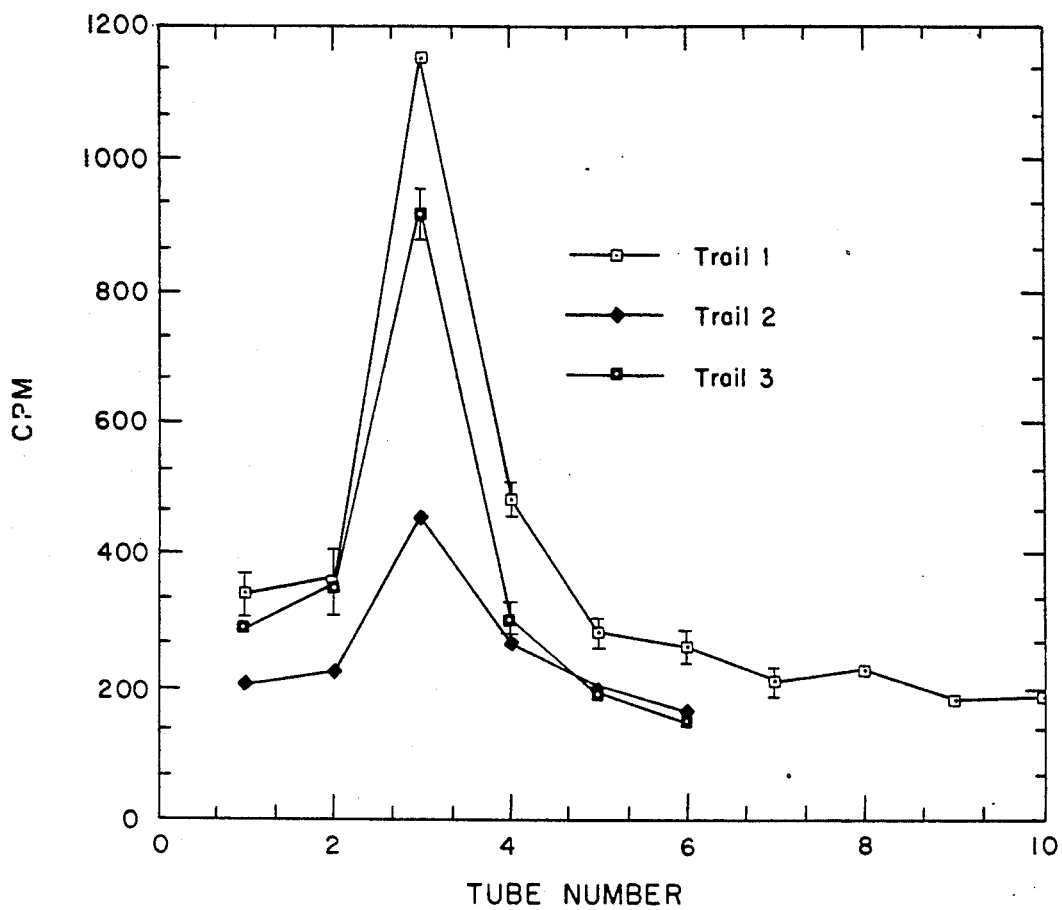
FIG. 3 is a chart demonstrating the displacement of labelled antigen by free antigen.

Initial studies to show that labelled dinitrophenol (DNP) could be displaced from the column by the free antigen DNP under continuous flow conditions used iodinated DNP-conjugate in order to most accurately quantitate the displacement. The data in FIG. 3 shows the displacement of the labelled antigen by low levels of free antigen. The amount of labelled antigen displaced after a second and third addition of antigen decreased, but was still measurable.

Figure 4:
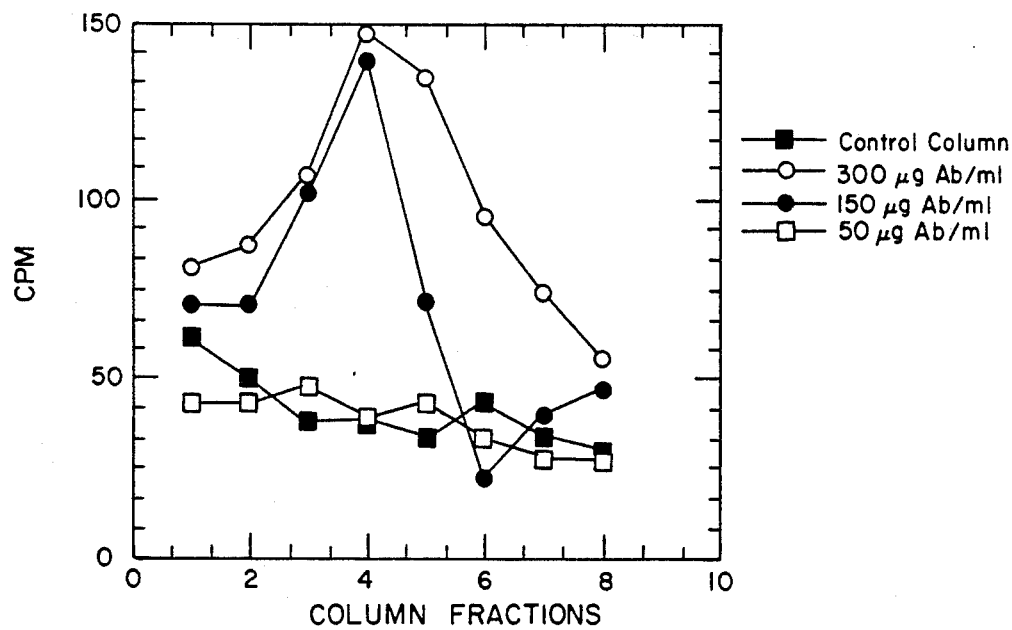
FIG. 4 is a graph demonstrating the effect of antibody density on the signal generation.
Figure 5:
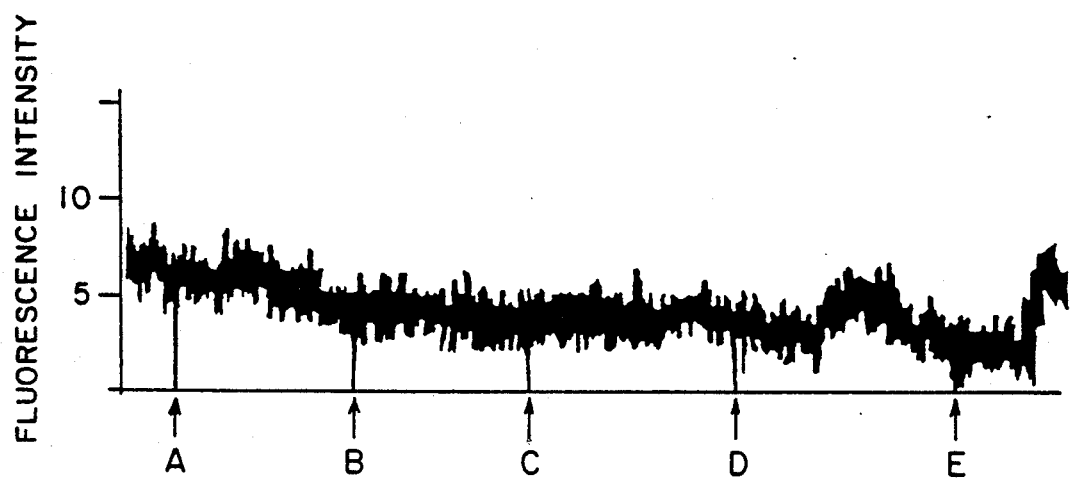
FIG. 5 is a reproduction of a strip chart record demonstrating the sensitivity for detection of a model antigen.

In order to increase the sensitivity of the detection, the conditions for running the system, as well as for fabricating the labelled antigen, were examined. System parameters tested included the density of antibodies on the solid support and the flow rate. Increased signal was seen with higher antibody density and consequently a higher density of immobilized antigen (FIG. 4). This probably reflects the increase in likelihood of the free antigen encountering the antibody/labelled antigen complex. The optimum flow rate for this particular antigen/antibody combination was approximately 0.3 ml/min (Table I). At 0.5 ml/minute, less labelled antigen was detected in the fluid downstream from the column. Decreasing the flow rate increased the number fluorescent antigens detected, but as the flow rate approached 0.1 ml/min, the labelled antigen became distributed over a larger volume and the fluorescence peaks broadened, making signal-to-noise resolution less accurate.

TABLE I

EFFECT OF FLOW RATE

| Flow Rate (ml/min) | Antigen (ng/ml) | Signal (Fluorescence Units) | Peak (h/w₁max) |
|---|---|---|---|
| 0.18 | 250 | 120 | 1.2 |
| 0.31 | 250 | 91 | 1.86 |

TABLE I-continued

EFFECT OF FLOW RATE

| Flow Rate (ml/min) | Antigen (ng/ml) | Signal (Fluorescence Units) | Peak (h/w₁max) |
|---|---|---|---|
| 0.53 | 250 | 45 | 5.0 |

For the system to be useful, it is essential that the displacement of the labelled antigen occur only in the presence of the specific target antigen. To ascertain the specificity of the reaction, compounds including insulin, glycine, lysine, sucrose, 0.1% TRITON ® X-100, and bovine serum albumin were introduced into the exchanger. None of these displaced the labelled antigen.

In a representative experiment, anti-DNP antibody coupled to SEPHAROSE ® was first mixed with radiolabelled DNP conjugate. After washing, 500 μl bed volume columns were prepared and various amounts at the antigen, DNP coupled to lysine (DNP-lysine), were introduced into the buffer stream and aliquots collected from the effluent for determination of radioactivity. Samples sizes ranged from a total of 4 ng to 12 ng DNP-lysine loaded on the column (Table II). At 4 ng DNP-lysine, the signal was less than 2×the background and this was determined to be the lower limit of detection for this assay.

TABLE II

DETECTION OF DNP USING RADIOLABELLED DNP-CONJUGATE

| [DNP-lys] (nM) | DNP-lys (ng) | Bkd (CPM) | Displaced Signal (CPM) | Signal/Bkd |
|---|---|---|---|---|
| 173 | 12 | 415 | 2391 | 5.8 |
| 115 | 8 | 255 | 1155 | 4.5 |
| 57 | 4 | 115 | 185 | 1.6 |

400 μl fractions were collected, and the activity determined on a scintillation counter. The peak activity is reported.

Similar to detecting the target antigen using radiolabelled signal molecule, it was shown that fluorophore-labelled signal molecule could also be used on this assay system. Columns of anti-DNP antibody coupled to SEPHAROSE ® were prepared. Instead of a radiolabel, a fluoresceinated DNP-conjugate was used as the signal molecule. Again varying amounts of DNP-lysine were loaded into the system (at 0.3 ml/min.), as well as lysine without DNP to serve as a specificity control. The smallest detectable sample size repeatedly achieved in these experiments was 20 ng DNP-lysine in 200 μl.

TABLE III

DETECTION OF DNP USING FLUORESCEINATED DNP-CONJUGATE

| Sample | Arbitrary Fluorescence Units | Signal:Noise Ratio |
|---|---|---|
| 200 ng lysine (Control) | not detected | 1 |
| 20 ng DNP-lys | 14 | 4.6 |
| 40 ng DNP-lys | 38 | 12.7 |
| 80 ng DNP-lys | 56 | 18.7 |
| 160 ng DNP-lys | 72 | 24 |

Finally, the level of sensitivity of the system in a flow configuration with the fluoresceinated/DNP antigen/antibody pair (antibody affinity is $10^{-7}$) was determined using the optimum flow rate of 0.35 ml/min. In a representative experiment, antigen could be detected at concentrations as low as 5 ng in 0.2 ml ($14 \times 10^{-12}$ moles). Higher concentrations of antigen generated a proportionately larger response up to the point where exhaustion of the labelled antigen from previous runs became apparent. It is notable, however, that a distinct positive signal was still generated when a 250 ng sample was added after previous additions of 25, 50, 100, and 250 ng antigen.

EXAMPLE 2

Detection of Trinitrotoluene (TNT)

A mouse monoclonal IgG antibody specific for TNT was immobilized on SEPHAROSE® 4B. The available antigen-binding sites were filled with fluoresceinated TNT-conjugate. This support was used to make a 200 μl bed-volume column. A buffer flow of phosphate buffered saline (PBS, 10 mM phosphate), pH 7.6, with 0.1% v/v TRITON® X-100 (PBS-TRITON®) was established. The effluent was directed to a Spectrovision portable fluorimeter and the fluorimeter output recorded on a strip chart recorder. After a stable baseline was obtained, a 200 μl sample of lysine at 8 μg/ml was loaded at the head of the apparatus to check the specificity of the system—no signal was obtained. Next, a 200 μl sample of a freshly prepared solution containing 200 ng TNT in PBS-TRITON® was introduced into the column. A signal greater than twice the baseline was consistently generated. The results are summarized in Table IV.

This example demonstrates that the approach of this invention can be used to specifically detect TNT in an aqueous sample.

TABLE IV

| | DETECTION OF TNT | |
|---|---|---|
| Sample | Arbitrary Fluorescence Units | Signal:Noise Ratio |
| 200 ng lysine (Control) | not detected | 1 |
| Run 1 | | |
| 96 ng TNT | 36 | 2.4 |
| 200 ng TNT | 85.5 | 3.8 |
| Run 2 | | |
| 200 ng TNT | 66 | 5.5 |

Detection of targets in continuous flow using fluorescence. Flow rate was 0.32 ml/min., bed volume was 200 μl.

EXAMPLE 3

Detection of Cocaine.

For the detection of cocaine, 200 μl bed-volume columns were established as above using anti-cocaine antibodies (Bio Design) and fluoresceinated benzoylecgonine. The assay was run under continuous flow conditions using the Spectrovision and an 8 μl flow cell. Various cocaine concentrations and sample volumes were applied to the column. The results, summarized in Table V, indicate that a challenge dose of less than 40 ng of cocaine can be detected by the immunosensor, with a signal-to-noise ratio of greater than 5-to-1, less than 20 seconds after sample introduction into the flow stream.

TABLE V

| DETECTION OF COCAINE SAMPLES IN CONTINUOUS FLOW | | |
|---|---|---|
| Sample | Arbitrary Units | Signal:Noise Ratio |
| 340 ng Lysine (Control) | not detected | 1 |
| 36 ng cocaine | 708 | 5.9 |
| 72 ng cocaine | 1870 | >20 |
| 144 ng cocaine | 2496 | >20 |

Column bed volume was 200 μl of antibody-coated SEPHAROSE®, and buffer flow rate was 0.72 ml/min.

In the flow immunosensor of this invention, there is no need to modify the antibody by the addition of fluorophores or proteolysis: such modifications can lead to loss of antibody activity and may affect the antibody affinity. Also, the weak antibody-antigen interactions, on which the hit-and-run system depends (Giese et al, ibid.), would not be productive in the continuous flow system as the labelled moiety would be washed out of the column as it was repeatedly released.

Obviously, many modifications and variations of the present invention are possible in light of the above teachings. It is therefore to be understood that, within the scope of the appended claims, the invention may be practiced otherwise than as specifically described.

What is claimed is:

1. A method of detecting a target comprising,
   (a) providing a solid phase-immobilized antibody capable of specifically binding to the target,
   (b) exposing an antigen binding site of the antibody to a labelled analog of the target to form a solid phase-immobilized, labelled antigen-antibody complex,
   (c) continuously flowing an aqueous medium suspected of containing the target past the solid phase-immobilized, labelled antigen-antibody complex at a flow rate allowing the target to displace the labelled analog from the labelled antigen-antibody complex under nonequilibrium conditions, and
   (d) detecting the displaced labelled analog, the amount of said displaced labelled analog being directly proportional to the concentration of said target in said medium.

2. The method according to claim 1 wherein the target is selected from the group consisting of thyroxine; high density lipoprotein; low density lipoprotein; cholesterol; albumin; alpha-1 antitrypsin; beta-2 microglobulin; ceruloplasmin; C1 inhibitor; C1q; C-reactive protein; cryfibrinogen; ferritin; myelin basic protein; transferrin; insulin; human chorionic gonadotropin; estrogen; progesterone; antigenic protein fragments from *H. influenza, N. meningitides, S. pneumonia, Bordetella pertussis, Borrelia burgdorferi*, pathogenic staphylococcus or pathogenic streptococcus; thephylline; digoxin; L-dopa; insulin; cocaine and its metabolites; cannabis metabolites; heroin; morphine metabolites; trinitrotoluene; cyclonite; pentaerythritol tetranitrate; nitrobenzene; and isothiocyanates.

3. The method according to claim 1 wherein the labelled antigen-antibody complex is soluble in said aqueous medium, and has one site per molecule at which the antibody of said complex is bound to the labelled antigen of said complex.

4. The method according to claim 3 wherein the label of the labelled complex is selected from the group consisting of radiolabels, fluorophores, chromophores, and electron spin labels.

5. The method according to claim 4 wherein the label of the labelled complex is selected from the group consisting of radiolabels and fluorophores.

6. The method according to claim 1 wherein the aqueous medium is an aqueous buffer.

7. The method according to claim 6 wherein the buffer is selected from the group consisting of phosphate-buffered saline, borate-buffered saline, TRIS-saline, Alseiver's solution and Ringer's solution.

8. The method according to claim 1 wherein the aqueous medium flows at a rate of about 0.1 to 2.0 milliliters per minute.

9. The method according to claim 3 wherein the aqueous medium flows at a rate of about 0.1 to 2.0 milliliters per minute.

10. The method according to claim 6 wherein the aqueous medium flows at a rate of about 0.1 to 2.0 milliliters per minute.

11. The method according to claim 10 wherein the aqueous medium flows at a rate of about 0.3 to 0.8 milliliters per minute.

12. The method of claim 1, wherein said solid phase is a flow-through bed.

* * * * *

UNITED STATES PATENT AND TRADEMARK OFFICE
CERTIFICATE OF CORRECTION

PATENT NO. : 5,183,740

DATED : February 2, 1993

INVENTOR(S) : Frances S. Ligler, Bruce P. Gaber, Ann W. Kusterbeck and Gregory A. Weimhoff It is certified that error appears in the above-identified patent and that said Letters Patent is hereby corrected as shown below:

Title page, Item 56 under the heading "Attorney, Agent or Firm" after "Barry A. Edelberg" add --; A. David Spevack --.

Signed and Sealed this

Twenty-fifth Day of January, 1994

Attest:

BRUCE LEHMAN

Attesting Officer

Commissioner of Patents and Trademarks